United States Patent [19]

Snyder

[11] Patent Number: 5,279,311

[45] Date of Patent: Jan. 18, 1994

[54] SUTURE SHUTTLE DEVICE

[75] Inventor: Stephen J. Snyder, Encino, Calif.

[73] Assignee: Linvatec Corporation, Largo, Fla.

[21] Appl. No.: 85,706

[22] Filed: Jun. 30, 1993

Related U.S. Application Data

[63] Continuation of Ser. No. 890,215, May 29, 1992, Pat. No. 5,250,053.

[51] Int. Cl.⁵ .............................................. A61B 17/00
[52] U.S. Cl. .................................... 128/898; 606/148
[58] Field of Search ............... 606/103, 139, 144, 145, 606/148, 185, 187, 222, 223, 224; 128/898; 223/102

[56] References Cited

U.S. PATENT DOCUMENTS

| | | | |
|---|---|---|---|
| 183,173 | 10/1876 | Jenkins | 223/102 |
| 279,693 | 6/1883 | Blinn . | |
| 386,723 | 7/1888 | Smith | 606/223 |
| 1,635,066 | 7/1927 | Wells . | |
| 1,856,721 | 5/1932 | Nagelmann . | |
| 2,897,820 | 8/1959 | Tauber | 606/224 |
| 3,233,800 | 2/1966 | Catania . | |
| 4,441,497 | 4/1984 | Paudler | 606/103 |
| 4,643,178 | 2/1987 | Nastari et al. | 606/103 |
| 4,779,616 | 10/1988 | Johnson . | |
| 4,781,190 | 11/1988 | Lee | 606/139 |
| 4,957,498 | 9/1990 | Caspari et al. . | |

*Primary Examiner*—Stephen C. Pellegrino
*Assistant Examiner*—Jeffrey A. Schmidt
*Attorney, Agent, or Firm*—Gene Warzecha

[57] ABSTRACT

A flexible, elongated suture passing device or shuttle capable of advancing monofilament or multi-stranded suture material to a remote work site. The suture shuttle is formed of a plurality of woven or braided fiber strands which are coated, over all but a central portion of the strands, with a material having a flexible exterior surface. A part of the central portion of the strands is formed into an eyelet for receiving a suture therethrough. A method is disclosed wherein one end of the suture shuttle is advanced to a work site until the eyelet passes through the tissue at the work site. This enables suture to be passed through the eyelet so the shuttle may be withdrawn to pass the suture back through the tissue to be sutured. Repeating this process brings any desired number of suture leads through the tissue so a knot may be tied.

3 Claims, 2 Drawing Sheets

SUTURE SHUTTLE DEVICE

This is a continuation application of application Ser. No. 07,890,215 filed May 29, 1992, now U.S. Pat. No. 5,250,053.

BACKGROUND OF THE INVENTION

1. Field of the Invention

This invention relates to medical devices and, in particular, to surgical instruments relating to suturing devices and techniques. More particularly this invention relates to devices and methods for passing sutures through tissue to be sutured.

2. Description of the Prior Art

It is often necessary in both open and endoscopic surgical procedures to use sutures to ligate, join or otherwise treat tissue. Generally, suture needles (with attached suture material) are grasped either manually or by forceps and passed through the desired work site so a knot can be tied. While the procedures are fairly straightforward in open surgery where most suture sites are readily accessible, in instances where access to the work site is not readily available and in endoscopic procedures the surgeon must use auxiliary devices to be able to grasp needles and pass them through desired tissue. The term "endoscopic" is used herein to mean surgical procedures performed through elongated cannulae inserted into a body through small incisions or punctures.

Several devices and methods for surgical repair requiring the passing of needles and sutures to distant (but not necessarily endoscopic) locations have already been developed. For example, U.S. Pat. No. 4,781,190 (Lee) discloses a method and a two-ended needle enabling arthroscopic suturing of the interior of a joint. The two-ended needle may be either straight or curved and has an eyelet intermediate the ends of the needle. Alternately passing the ends of the needle through tissue to be sutured enables a suture, passing through the eyelet of the needle, to be woven through the tissue.

U.S. Pat. No. 4,441,497 (Paudler) discloses a suture passer having a plurality of flexible elongated members joined at their ends, these ends being sharpened enough to pass through desired tissue sites. Pushing the ends toward each other opens up spaces between the members into which one or more sutures may be placed. Moving the ends of the flexible members away from each other closes up the spaces to thereby grip the sutures so the ends of the flexible members and, consequently, the sutures, may be passed through desired suture sites.

Each of the foregoing suture passing devices has disadvantages associated with it and it is an object of this invention to overcome these disadvantages. In particular, it is an object of this invention to produce a suture passing device which is more flexible than prior art devices while also being strong enough to be directed to work sites deep within the body. The invention is flexible enough to be directed in any desired direction and strong enough to pull sutures from outside the body to the desired work site. The suture may then be tied and the suture knot advanced to the suture site by known techniques.

Other devices known to advance suture material directly to a work site are shown in U.S. Pat. Nos. 4,890,615 (Caspari et al.) and 4,923,461 (Caspari et al.), both of which are incorporated by reference herein.

The Caspari devices and others like them advance suture material by passing it through one or more rollers, one of which is turned by the user to propel the suture beyond the nip of the rollers. While suitable for monofilament suture, such roller-type devices may unravel multi-stranded suture which is preferable for certain applications. Accordingly, a means of passing multi-stranded suture material via roller-type suture passing devices would be desirable. It is an object of this invention to produce a suture passing device or shuttle that is usable with roller-type suture advancing devices and suitable for passing multi-stranded suture with such devices.

SUMMARY OF THE INVENTION

These and other objects of the invention are achieved by the preferred embodiment disclosed herein which is a suture shuttle device comprising a flexible, wire-like member having a predetermined length and a flexible eyelet secured to the wire-like member intermediate its ends. The wire-like member is formed of a plurality of braided strands of wires, fibers or the like, the strands being separated at a central point to form the eyelet. The device is coated on either end of the eyelet with a flexible protective coating material to prevent the strands from unravelling during use.

As will be further described below, the preferred embodiment disclosed herein is also used to practice a method of endoscopic suturing with a multi-stranded suture.

DESCRIPTION OF THE PREFERRED EMBODIMENT

Figure 1:
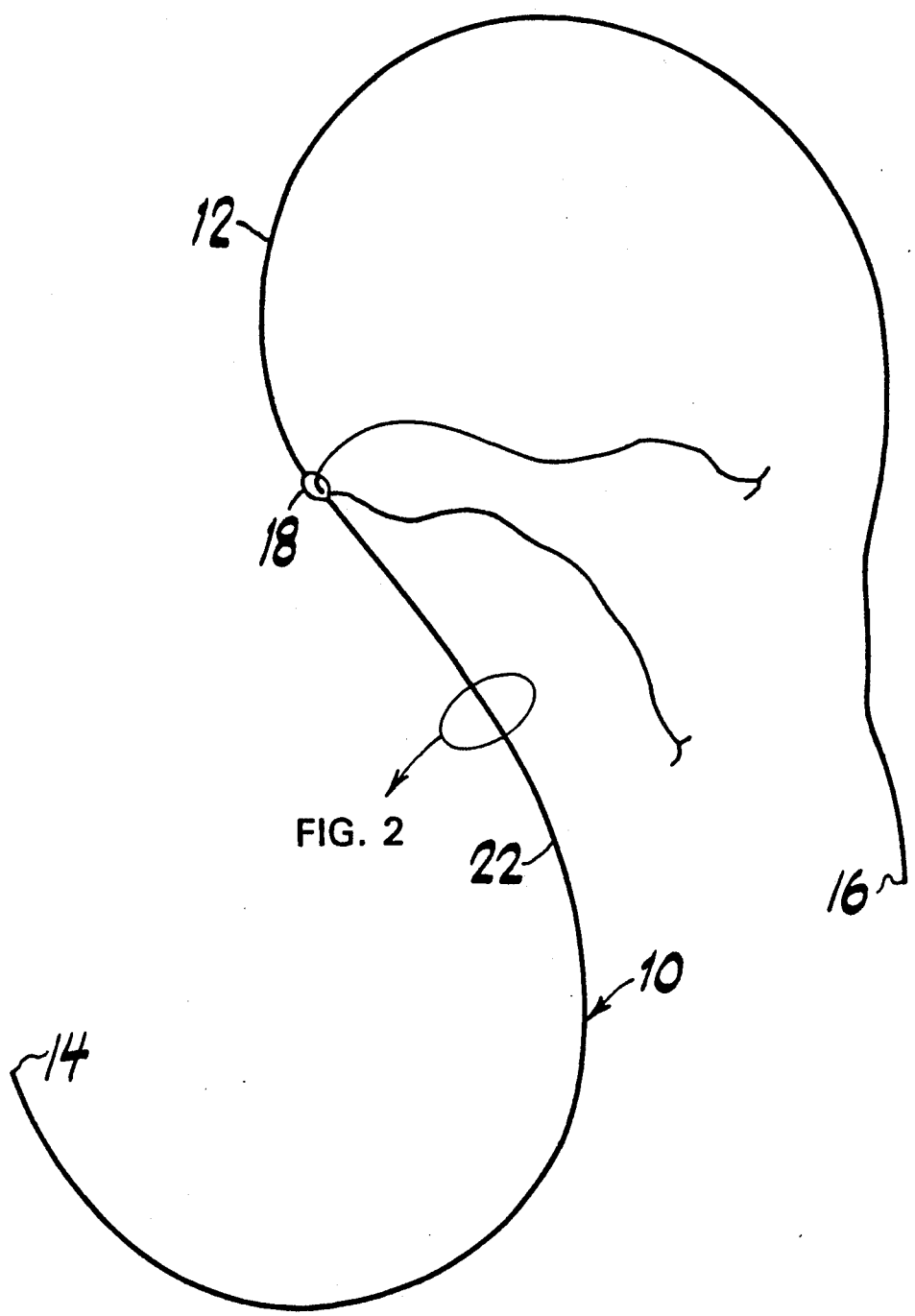
FIG. 1 is a diagrammatic view of a suture passing device constructed in accordance with the principles of this invention.

Referring now to FIG. 1 there is shown a suture passing device or shuttle 10 constructed in accordance with the principles of this invention. Suture shuttle 10 comprises an elongated flexible member 12 having ends 14 and 16 and an intermediate eyelet portion 18.

Figure 2:
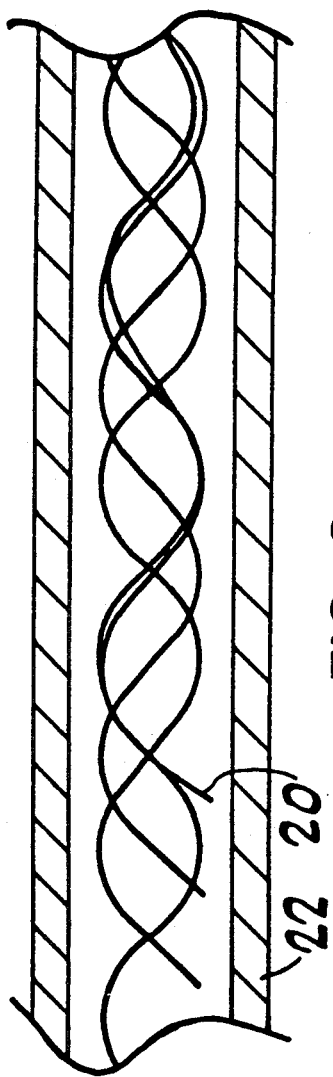
FIG. 2 is a diagrammatic view of an exploded portion of the suture passing device shown in FIG. 1.

In the preferred embodiment, elongated member 12 is formed of a plurality of woven or braided wires or fibers 20, best seen in FIG. 2. The term "wires" is used generically because wires 20 may be any wire-like materials provided they are sterilizable, flexible and strong enough for the intended applications. The wires are coated over a portion of the length of shuttle 10 with a flexible coating 22 such as Teflon ®, nylon, polyurethane and the like. It will be understood that coating 22 may fill the interstices between wires 20 and serves to provide shuttle 10 with a firm but flexible exterior surface so it may be more easily advanced to a work site as will be understood below. The coating 22 should be firm enough to enable the shuttle to be easily passed through and advanced by the roller feeding mechanism of prior art roller-type devices without unraveling the braided wires. As best seen in FIG. 1, coating 22 is applied to the full length of shuttle 10 with the exception of an intermediate (approximately 10 mm) portion within which eyelet 18 is situated. Eyelet 18 may be positioned closer to one of the ends 14, 16 if necessary for certain applications. In the preferred embodiment eyelet 18 is formed by separating braided wires 20 from each other to form an opening. It will be understood that eyelet 18 may be formed in any other manner provided the eyelet is sufficiently flexible to perform the functions identified below. For example, if shuttle 10 were formed of a single monofilament strand, eyelet 18 could be a separate member attached to the single strand intermediate its ends Preferably, eyelet 18 should be flexible enough to enable it to be deformed enough to pass through tissue as well as narrow openings, as will be understood below.

One or both of ends 14 and 16 may be sharpened or otherwise provided with a needle point if shuttle 10 is intended to pass suture through tissue without the aid of any auxiliary device having a needle point. The sharpened ends could be formed by shaping coating 22 at ends 14, 16 into pointed tips, or otherwise affixing sharpened tips to the body of member 12. However, as will be described below, a preferred method of using the invention is to leave the ends unsharpened and use shuttle 10 in combination with endoscopic cannulae to shuttle a suture 30 from one location to another.

The method of using shuttle 10 descried herein stems from the goal of threading preferably multi-stranded suture through body tissues which are accessible only through one or more endoscopic cannulae. One preferred method of using shuttle 10 will be described in the context of arthroscopically suturing a ligament to a suture anchor. It should be understood, however, that the described method is easily adaptable to other endoscopic applications.

Figure 3:
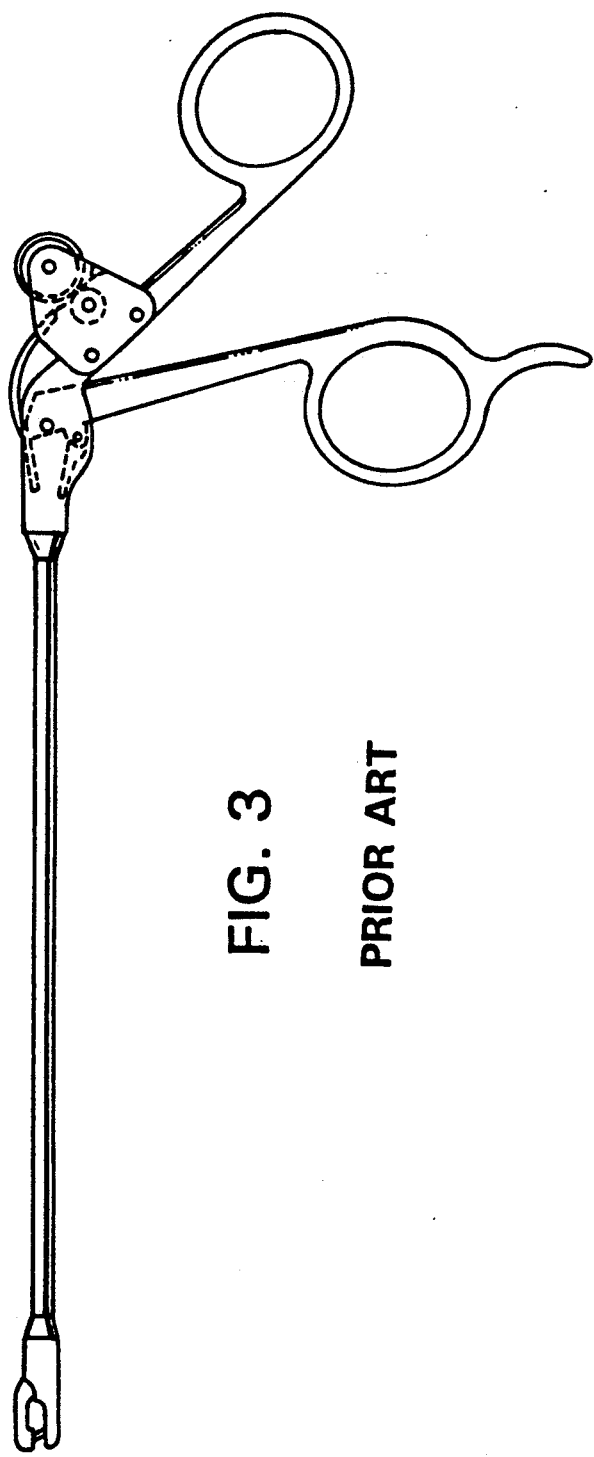
FIG. 3 is a side elevational view of a prior art, roller-type suture passing device.

In arthroscopic ligament suturing a primary cannula is inserted, for example, in the anterior part of the body joint so visualization of the suture site may be achieved using conventional means. Once a suture site is identified, a suture anchor may be conventionally inserted through the primary anterior cannula and embedded in a body substrate surface to which a ligament will be sutured. One type of suitable suture anchor is known as the STATAK TM Soft Tissue Attachment Device described in U.S. Pat. No. 4,632,100 and sold by Zimmer, Inc. Warsaw, Ind. After the suture anchor with suture is driven into the bone, two suture leads attached to the anchor extend out of the primary anterior cannula. A secondary, posterior cannula is then placed into the joint and the two suture leads are grasped by a hook or suture retrieval forceps, inserted through the secondary posterior cannula, and pulled back through the primary cannula and out of the secondary cannula. Subsequently, a roller-type suture punch such as that shown in FIG. 3, which is the subject of aforementioned U.S. Pat. No. 4,890,615 (Caspari et al.), is inserted into the primary cannula. A suture shuttle 10 is threaded into the punch and then advanced to the suture site in a conventional manner. The tissue which is intended to be reattached is pierced by the suture punch and the shuttle 10 is fed into the joint enough to extend from the tip of the suture punch a sufficient distance to enable the end (14 or 16) to be grasped by a forceps inserted through the posterior cannula. Shuttle 10 is then pulled through the posterior cannula enough to expose eyelet 18 such that the shuttle now extends through the posterior cannula (along with the two suture ends) and the anterior cannula. The length of shuttle 10 may be changed if necessary for different applications. One of the suture ends is then passed through eyelet 18 and the suture shuttle is then pulled back out the primary cannula, thus bringing one suture lead through the tissue to be sutured. The process is then repeated with the suture shuttle again threaded through the suture punch which is then punched through a different location (spaced from the first) and the suture shuttle is advanced until it may again be grasped through the secondary cannula. The suture shuttle is again pulled through the secondary cannula until the eyelet is exposed and the second suture end is passed through the eyelet. The suture shuttle is then pulled back through the primary cannula so that both ends of the suture attached to the anchor now pass through tissue to be sutured and are accessible through the primary cannula. The suture ends may now be tied in a conventional manner.

It will be understood by those skilled in the art that numerous modifications and improvements may be made to the preferred embodiment of the invention described herein without departing from the spirit and scope thereof.

What is claimed is:

1. A method of endoscopically suturing tissue within a body comprising the steps of:
    (a) penetrating the tissue to be sutured with a hollow needle having a distal end adjacent said tissue and a proximal end outside the body;
    (b) providing a flexible, elongated wire-like member having a predetermined length and an eyelet secured to said flexible wire-like member intermediate its ends;
    (c) advancing one end of said flexible wire-like member through said hollow needle until the eyelet exits from the distal end of said hollow needle while the other end of said flexible wire-like member extends from the proximal end of said needle;
    (d) pulling said one end of said flexible wire-like member outside of the body until the eyelet is outside of the body;
    (e) threading one end of a length of suture through said eyelet;
    (f) withdrawing said other end of said flexible wire-like member and said threaded suture end from said hollow needle to thereby pass said threaded suture end through said tissue while leaving the other end of said suture accessible outside the body;
    (g) removing said hollow needle from said tissue;
    (h) removing said threaded suture end from said eyelet;
    (i) tying a knot with said suture ends.

2. A method according to claim 1 wherein said suture is multi-stranded.

3. A method of endoscopic suturing of tissue within the body comprising the steps of:
    penetrating tissue to be sutured with a hollow needle;
    feeding through the hollow needle a flexible, elongated wire-like member having an eyelet intermediate its end to cause said eyelet to extend from the hollow needle;
    withdrawing the hollow needle from the tissue and from the body;
    pulling said eyelet from the body while leaving said flexible, wire-like member within said tissue;
    threading a suture end through said eyelet;
    pulling said eyelet with the threaded suture end back through the tissue;
    removing said flexible, wire-like member;
    tying a knot in the suture material.

* * * * *